US008969650B2

(12) United States Patent
Goda et al.

(10) Patent No.: US 8,969,650 B2
(45) Date of Patent: Mar. 3, 2015

(54) BODILY FLUID-ABSORBENT STRUCTURE (75) Inventors: Hiroki Goda, Kanonji (JP); Satoshi Mizutani, Kanonji (JP); Kou Detani, Kanonji (JP)

(73) Assignee: Unicharm Corporation, Ehime (JP)

( * ) Notice: Subject to any disclaimer, the term of this patent is extended or adjusted under 35 U.S.C. 154(b) by 342 days.

(21) Appl. No.: 13/636,031

(22) PCT Filed: Mar. 31, 2011

(86) PCT No.: PCT/JP2011/001975
§ 371 (c)(1),
(2), (4) Date: Sep. 19, 2012

(87) PCT Pub. No.: WO2011/122055
PCT Pub. Date: Oct. 6, 2011

(65) Prior Publication Data
US 2013/0023845 A1    Jan. 24, 2013

(30) Foreign Application Priority Data
Mar. 31, 2010   (JP) .................................. 2010-084216

(51) Int. Cl.
*A61F 13/534*    (2006.01)
*A61F 13/531*    (2006.01)
*A61F 13/53*     (2006.01)

(52) U.S. Cl.
CPC ... *A61F 13/531* (2013.01); *A61F 2013/530007* (2013.01); *A61F 2013/530598* (2013.01)
USPC .......................................... 604/374; 604/375

(58) Field of Classification Search
CPC ............................. A61F 13/534; A61F 13/531
USPC ................................................ 604/374, 375
See application file for complete search history.

(56) References Cited

U.S. PATENT DOCUMENTS

| 4,610,678 | A | 9/1986 | Weisman et al. |
|---|---|---|---|
| 2004/0015144 | A1 | 1/2004 | Mori et al. |
| 2005/0137547 | A1* | 6/2005 | Didier Garnier et al. ..... 604/375 |
| 2007/0299416 | A1 | 12/2007 | Noda et al. |
| 2008/0001919 | A1* | 1/2008 | Pascucci ...................... 345/163 |
| 2010/0022978 | A1 | 1/2010 | Kasai et al. |

FOREIGN PATENT DOCUMENTS

| JP | 2002172139 | 6/2002 |
|---|---|---|
| JP | 2007236864 | 9/2007 |
| JP | 2008125604 | 6/2008 |

OTHER PUBLICATIONS

Extended European Search Report issued Feb. 6, 2014, corresponds to European patent application No. 11762296.9.
International Search Report and Written Opinion for PCT/JP2011/001975 mailed Jun. 14, 2011.

* cited by examiner

*Primary Examiner* — Tatyana Zalukaeva
*Assistant Examiner* — Sara Sass
(74) *Attorney, Agent, or Firm* — Lowe Hauptman & Ham LLP (57) ABSTRACT The present invention provides a bodily fluid-absorbent structure improved so as to facilitate bodily fluids to disperse in a thickness direction of the structure. Core material of a bodily fluid-absorbent structure is formed of an aggregation of fluff wood pulp fibers. The aggregation has a basis mass in a range of 150 to 500 g/m² and a specific volume in a range of 3 to 20 cc/g. In the aggregation, a relationship between horizontal orientation index $I_H$ and specific volume VSP of fluff wood pulp fibers is represented by a formula as follows:

$I_H$ is less than or equal to $-0.099$VSP$+2.4$.

7 Claims, 9 Drawing Sheets

BODILY FLUID-ABSORBENT STRUCTURE

RELATED APPLICATIONS

The present application is a national phase of PCT/JP2011/001975, filed Mar. 31, 2011 and is based on, and claims priority from, Japanese Application Number 2010-084216, filed Mar. 31, 2010.

TECHNICAL FIELD

The present disclosure relates to a bodily fluid-absorbent structure suitable to be used in a disposable bodily fluid-absorbent article, such as a disposable diaper or a disposable menstruation napkin.

RELATED ART

It is known to use an aggregation of fluff wood pulp fibers or an aggregation of fluff wood pulp fibers and super-absorbent polymer particles as a core material in a bodily liquid-absorbent structure for disposable diapers or menstruation napkins. It is also known to use a roll press to compress such aggregation to thereby obtain a well thinned core material.

For example, U.S. Pat. No. 4,610,678 A (PATENT DOCUMENT 1) discloses high-density absorbent structures obtained by mechanically compressing a mixture of hydrophilic fibers and super-absorbent polymer particles.

JP 2002-172139 A (PATENT DOCUMENT 2) exemplarily discloses a bodily-fluid absorbent structure obtained by treating liquid-absorbent fibers, such as wood pulp fibers, and super-absorbent polymer (SAP) particles by a so-called air-lay method comprising using a spray chute and a suction unit so that fiber refinement and mixing thereof with the SAP particles may concurrently occur, thereby accumulating such mixture on a belt conveyor and compressing the mixture of fibers and SAP particles by a pressure roll to a desired thinness.

CITATION LIST

Patent Literature

[PATENT DOCUMENT 1] U.S. Pat. No. 4,610,678 A
[PATENT DOCUMENT 2] JP 2002-172139 A

SUMMARY OF INVENTION

Problem to be Solved by the Invention

Compression of an aggregation of wood pulp fibers or an aggregation of wood pulp fibers and super-absorbent polymer particles using a press or pressure rolls causes the aggregation to be densified, thereby thinned. However, the inventors have noted that, simultaneously, such compression is liable to orient the longitudinal direction of wood pulp fibers sideways. In other words, the longitudinal direction of wood pulp fibers is generally oriented not in the thickness direction of the core material in the bodily fluid-absorbent structure, but in the direction which is orthogonal to the thickness direction. In the bodily fluid-absorbent structure including such core material aggregation, bodily fluids have a high propensity of planarly dispersing in the vicinity of the structure's inner surface. In contrast, if bodily fluids disperse in the thickness direction of the structure, bodily fluids staying on the inner surface of the structure can be effectively reduced to eliminate or to alleviate the wearer's discomfort due to bodily fluids staying on the inner surface, i.e., in contact with the wearer's skin.

Measure to Solve the Problem

One or more aspects of the present invention is characterized in a bodily fluid-absorbent structure comprising liquid-absorbent material formed of an aggregation of fluff wood pulp fibers and having an inner surface and an outer surface, a liquid-pervious sheet covering the inner surface, and a liquid-pervious or liquid-impervious sheet covering the outer surface.

In this bodily fluid-absorbent structure, the aggregation has a basis mass in a range of 150 to 500 g/m² and a specific volume in a range of 3 to 20 cc/g, and a relationship between a horizontal orientation index $I_H$ and the specific volume VSP of the fluff wood pulp in the aggregation is represented by the following formula:

$I_H$ is less than or equal to $-0.099 \text{VSP} + 2.4$.

The horizontal orientation index $I_H$ is a value obtained according to the following formula:

$$I_H = CS_1/((CS_2+CS_3)/2),$$

wherein $CS_1$ represents an average cross-sectional area of the fluff wood pulp fibers observed on a cross-section extending in parallel to a horizontal plane when the outer surface of the aggregation is placed on the horizontal plane, $CS_2$ and $CS_3$ represent average cross-sectional areas of the fluff wood pulp fibers observed on two cross-sections extending orthogonally to each other and to the horizontal plane.

DETAILED DESCRIPTION OF THE PREFERRED EMBODIMENTS

Details of a bodily fluid-absorbent structure according to exemplary embodiments of the present invention will be more fully understood from the description given hereunder in reference to the accompanying drawings.

Figure 1:
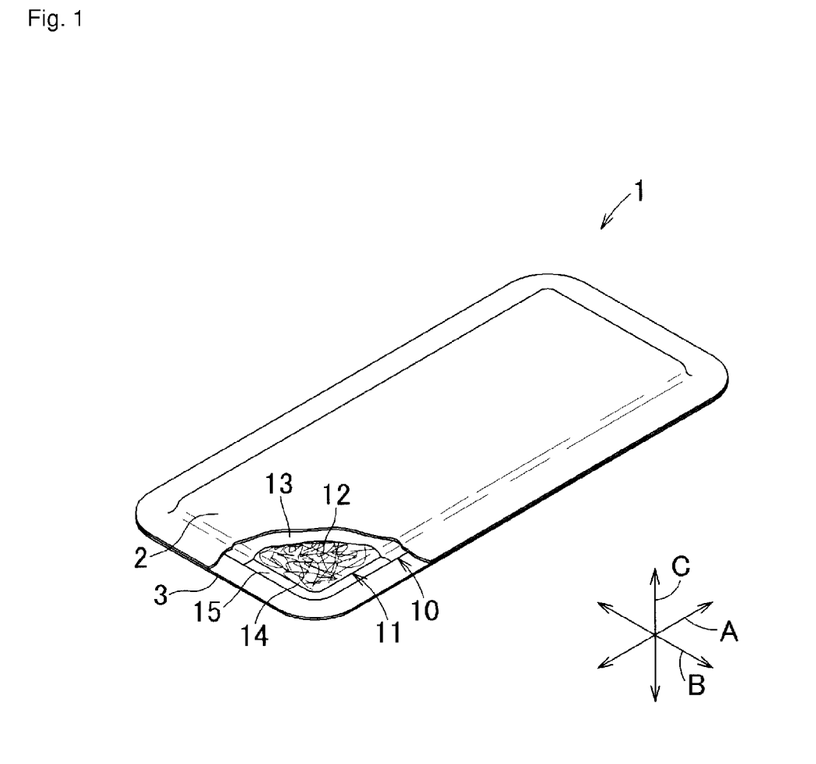
FIG. 1 is partially cutaway perspective view of a menstruation napkin.

Referring to FIG. 1, a disposable bodily fluid-absorbent article, e.g., a menstruation napkin 1, comprises a liquid-pervious topsheet 2, a liquid-impervious backsheet 3 and a bodily fluid-absorbent structure 10 sandwiched between the top- and backsheets 2, 3, wherein a longitudinal direction, a transverse direction and a thickness direction are designated by double-headed arrows A, B and C, respectively. The topsheet 2 and the backsheet 3 extend outward beyond a peripheral edge of the bodily fluid-absorbent structure 10 and are bonded together outside the peripheral edge, e.g., by hot melt adhesives (not shown). The bodily fluid-absorbent structure 10 comprises a liquid-absorbent core material 11, a liquid-pervious cover sheet 13 covering an inner side 12 of the core material 11, and a liquid-pervious or liquid-impervious cover sheet 15 covering an outer side 14 of the core material 11, wherein the cover sheets 13, 15 extend outward beyond a peripheral edge of the core material 11 and are bonded together, e.g., by means of hot melt adhesive (not shown), or merely overlap each other without being bonded. The term "inner side" used herein means the side of the menstruation napkin 1 facing the wearer (not shown) of the menstruation napkin 1, and the term "outer side" used herein means the side of the menstruation napkin 1 facing the wearer's garment (or facing away from the wearer).

In such menstruation napkin 1, as the topsheet 2, a liquid-pervious sheet, such as a nonwoven fabric of thermoplastic synthetic fibers or a plastic film may be used. As the backsheet 3, for example, a liquid-impervious plastic film, a liquid-impervious nonwoven fabric of thermoplastic synthetic fibers, or a liquid-impervious laminate of a plastic film and a nonwoven fabric may be used. As the cover sheet 13, for example, liquid-pervious tissue paper or a liquid-pervious nonwoven fabric of thermoplastic synthetic fibers may be used. As the cover sheet 15, not only a liquid-pervious sheet similar to the cover sheet 13 but also a liquid-impervious plastic film may be used.

Figure 2:
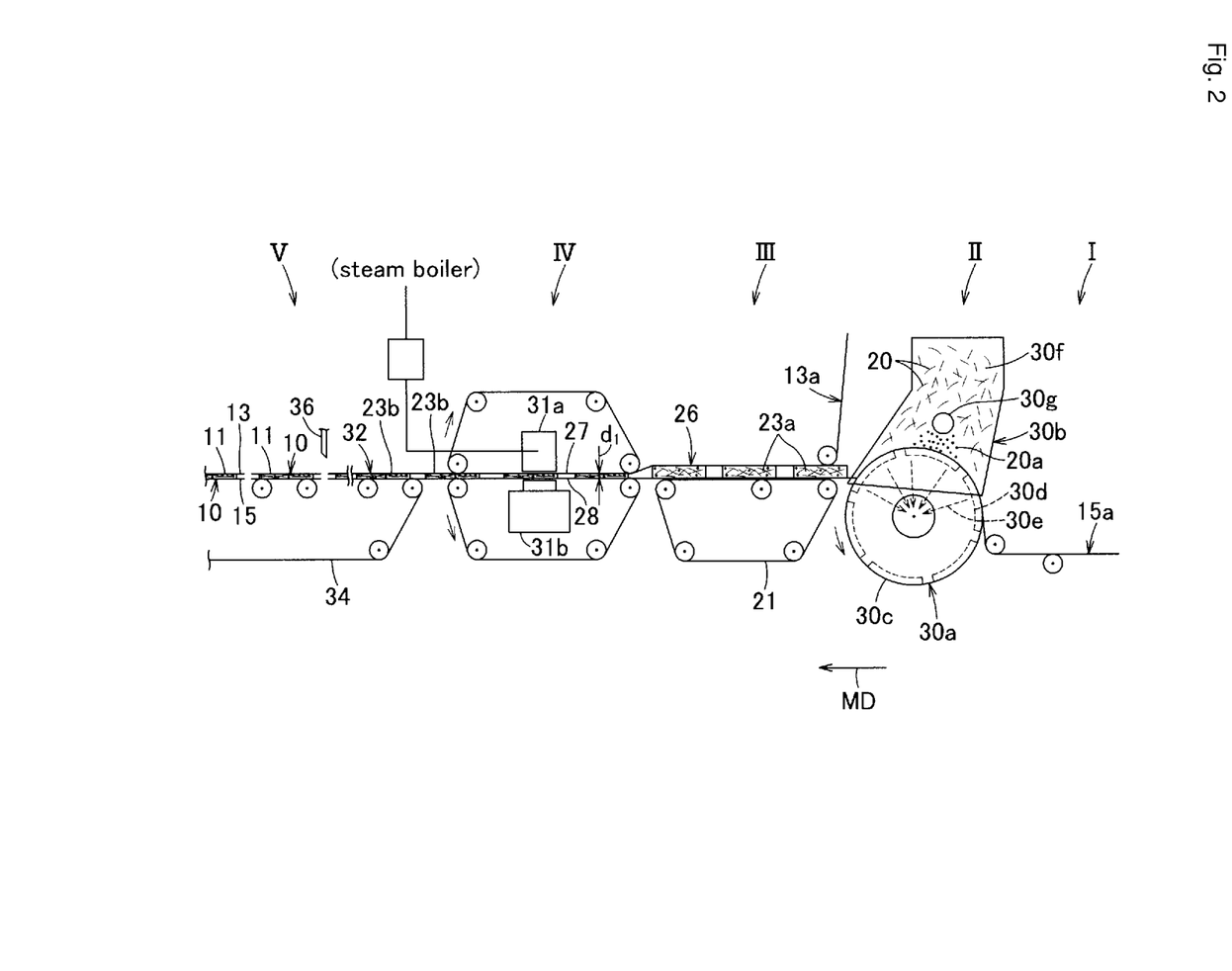
FIG. 2 is a diagram schematically illustrating a process for making a bodily fluid-absorbent structure.

Referring to FIG. 2, a process for making bodily fluid-absorbent structures, such as the bodily fluid-absorbent structure 10, will be described. In a first step I, a carrier sheet web 15a for forming cover sheets 15 is continuously fed from the upstream side in a machine direction MD.

In a second step II, a suction drum 30a rotating in a counterclockwise direction MD and a liquid-absorbent material feed region 30b provided with a hood shape to cover the suction drum 30a are involved. The suction drum 30a is formed on its peripheral surface 30c with a plurality of depressions 30d each having a shape generally the same as the planar shape of the individual core material 11 arranged at a predetermined pitch in a circumferential direction of the suction drum 30a. The respective depressions 30d successively move into the feed region 30b as the suction drum 30a rotates and thereupon these depressions 30d are successively subjected to a suction effect of vacuum. The feed region 30b feeds fluff wood pulp fibers 20 refined by a sawmill type fiber refiner (not shown) to the suction drum 30a and includes a fluff wood pulp fiber feeder 30f and, if desired, a feeder 30g for feeding super-absorbent polymer particles 20a. In this way, it is possible for the feed region 30b to feed the depression 30d moving into this region 30b with fluff wood pulp fibers 20, or concurrently with both fluff wood pulp fibers 20 and super-absorbent polymer particles 20a so as to be mixed together or to be laminated one upon another. The carrier sheet web 15a running from the step I is put on the peripheral surface 30c of the suction drum 30a and thereupon the carrier sheet web 15a is deformed in accordance with the shape of the depression 30d to cover the surface of the depression 30d. Thereafter, the depression 30d is fed with fluff wood pulp fibers 20, or concurrently fed with both fluff wood pulp fibers 20 and super-absorbent polymer particles 20a.

In a third step III, the carrier sheet web 15a is transferred from the suction drum 30a onto a first endless belt 21 and runs in the machine direction MD. On the carrier sheet web 15a, a plurality of first wood pulp fiber units 23a are arranged intermittently in the machine direction MD. Each of the first wood pulp fiber units 23a corresponding to the individual core material 11 and shaped in accordance with the shape of the depression 30d is formed by the aggregation of fluff wood pulp fibers 20, or the aggregation of both fluff wood pulp fibers 20 and super-absorbent polymer particles 20a still in a un-compressed state. In this third step III, a cover sheet web 13a for forming cover sheets 13 is continuously fed from above as viewed in FIG. 2 and cooperates with the carrier sheet web 15a to sandwich the first wood pulp fiber units 23a in between, to thereby form a first composite laminate web 26 comprising the cover sheet web 13a, the carrier sheet web 15a and the first wood pulp fiber units 23a.

In a fourth step IV, the first composite laminate web 26 is fed into a gap defined between an air-permeable second endless belt 27 and an air-permeable third endless belt 28 running in parallel to each other in the machine direction MD. These second and third endless belts 27, 28 are spaced from each other in a vertical direction as viewed in FIG. 2 by a distance $d_1$ preset to a desired dimension. A nozzle assembly 31a adapted to inject pressurized steam jets is installed immediately above the second endless belt 27 and a suction box 31b is installed below the third endless belt 28 so as to face the nozzle assembly 31a. In one example of the nozzle assembly 31a, a plurality of nozzles (not shown) each having a nozzle diameter of 0.5 mm are arranged in a cross direction CD (See FIG. 3) which is orthogonal to the machine direction MD at a pitch of 2 mm. The nozzle assembly 31a has a dimension in its cross direction CD larger than a direction of the first composite laminate web 26 in its cross direction CD so that the first composite laminate web 26 may be injected over its entire width with pressurized steam jets. Steam jets at a high-pressure at a level of 0.7 Mpa is injected from the respective nozzles at a rate of 1.27 kg/m$^2$ to the first wood pulp fiber units 23a in the first composite laminate web 26 running, for example, at a rate of 5 m/min and, in consequence, the first composite laminate web 26 is transformed into a second composite laminate web 32 which is, in turn, transferred onto fourth endless belt 34 in a fifth step V.

In the fifth step V, the second composite laminate web 32 is cut between each pair of the adjacent second wood pulp fiber units 23b, 23b in the machine direction MD to obtain the individual bodily fluid-absorbent structures 10 comprising the core material 11 transformed from the second wood pulp fiber unit 23a, the cover sheet 15 transformed from the carrier sheet web 15a and the cover sheet 13 transformed from the cover sheet web 13a.

In the bodily fluid-absorbent structure 10 obtained by the process exemplarily described with respect to FIG. 2, fluff wood pulp fibers 20 air-conveyed and laminated to form the first wood pulp fiber units 23a in the second step II is injected with high-pressure steam in the third step III and, in consequence, the longitudinal direction of fluff wood pulp fibers 20 is forced by the steam jets to extend from the cover sheet web 13a toward the carrier sheet web 15a, i.e., to be oriented in the thickness direction of the first wood pulp fiber unit 23a. In accordance with one or more embodiments of the present invention, a degree of such reorientation may be adjusted by appropriately selecting the injection condition(s) of high-pressure steam jets and the distance $d_1$ between the second and third endless belts 27, 28. When it is desired to use the liquid-impervious sheet as the cover sheet 15 for the core material 11, the liquid-pervious carrier sheet web 15a may be exchanged with a liquid-impervious sheet web or a liquid-impervious sheet web may be lapped over the carrier sheet web 15a in the fifth step V in FIG. 2. When it is desired to feed the super-absorbent polymer particles together with fluff wood pulp fibers in the second step II, a quantity of the super-absorbent polymer particles is preferably in a range of 10 to 80% of total mass of fluff wood pulp fibers in each first wood pulp fiber unit 23a.

Figure 3:
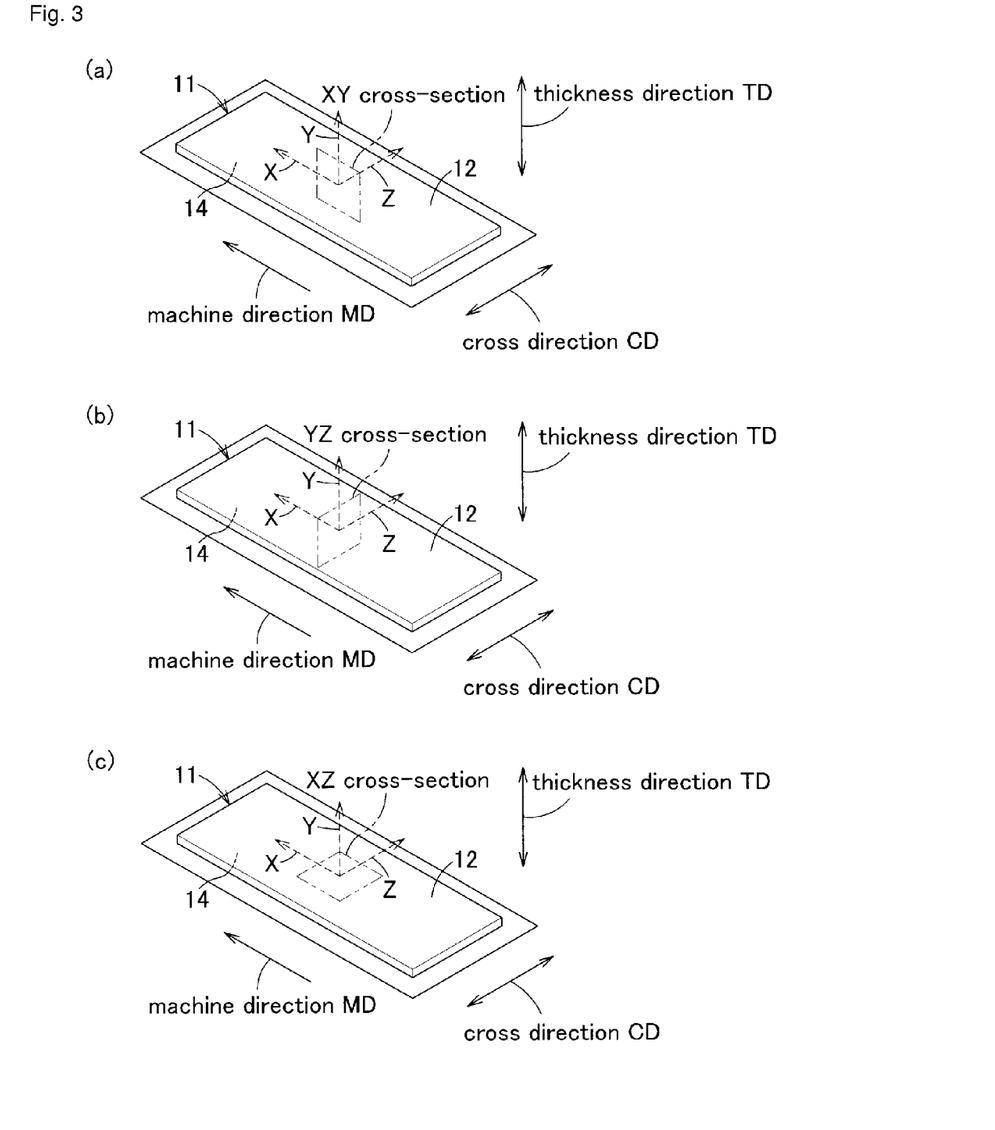
FIG. 3 includes diagrams showing sections of various bodily fluid-absorbent structures to be X-ray CT photographed.

FIG. 3 includes a series of diagrams to explain a method of observing an orientation state of fluff wood pulp fibers 20 in the core material 11 of the bodily fluid-absorbent structure 10 and, in the series of diagrams, the outer surface of the core material 11 is placed on a horizontal plane (not shown). In accordance with one or more embodiments of the present invention, X-ray CT (X-ray Computed Tomography) photographs of the core material 11 are used to observe the orientation state of fluff wood pulp fibers 20. To prepare such X-ray CT photographs, cross-sections of the core material 11 to be photographed are selected and the selected cross-sections are fully photographed. Then, the cross-sectional areas of the respective fibers of the fluff wood pulp fibers 20 appearing in the cross-sections are measured. On the basis of the result of measurement, an average cross-sectional area per component fibers is determined.

FIG. 3(a) indicates a position of a cross-section of the core material 11 to be X-ray CT photographed, the cross-section extending in parallel to the machine direction MD (hereinafter referred to as XY cross-section).

FIG. 3(b) indicates a position of a cross-section of the core material 11 to be X-ray CT photographed, the cross-section extending in parallel to the cross direction CD (hereinafter referred to as YZ cross-section). The cross direction CD extends orthogonally to the machine direction MD in FIG. 2 and in the transverse direction of the first composite laminate web 26.

FIG. 3(c) indicates a position of a cross-section of the core material 11 to be X-ray CT photographed, the cross-section extending in parallel to the inner surface 12 (See FIG. 1) (hereinafter referred to as XZ cross-section). This XZ cross-section is a plane extending in parallel to the outer surface 14.

Figure 4:
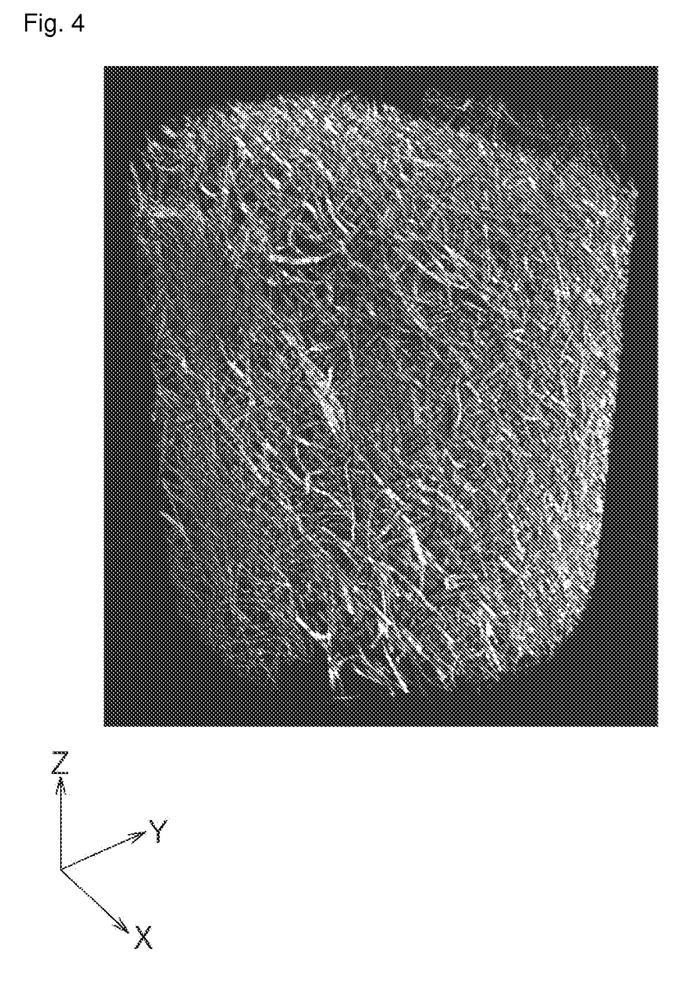
FIG. 4 is an exemplary X-ray CT photo.
Figure 5:
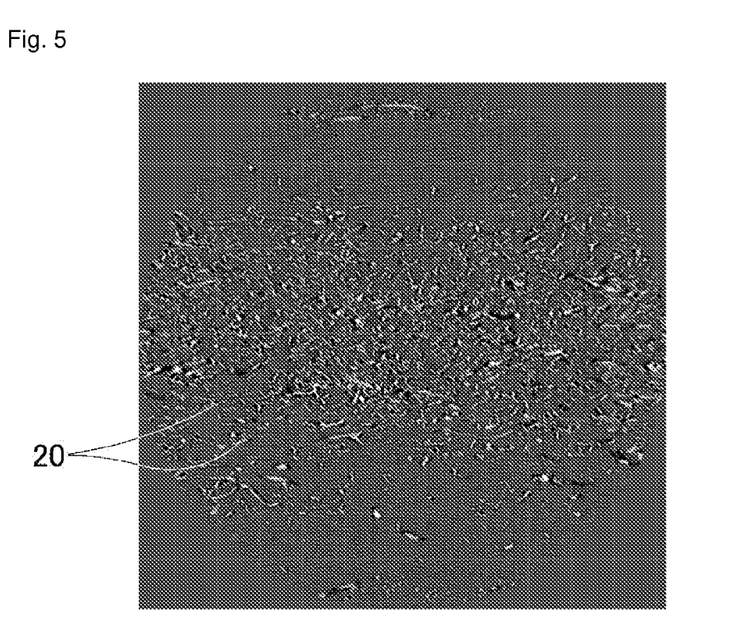
FIG. 5 is another exemplary X-ray CT photo.
Figure 6:
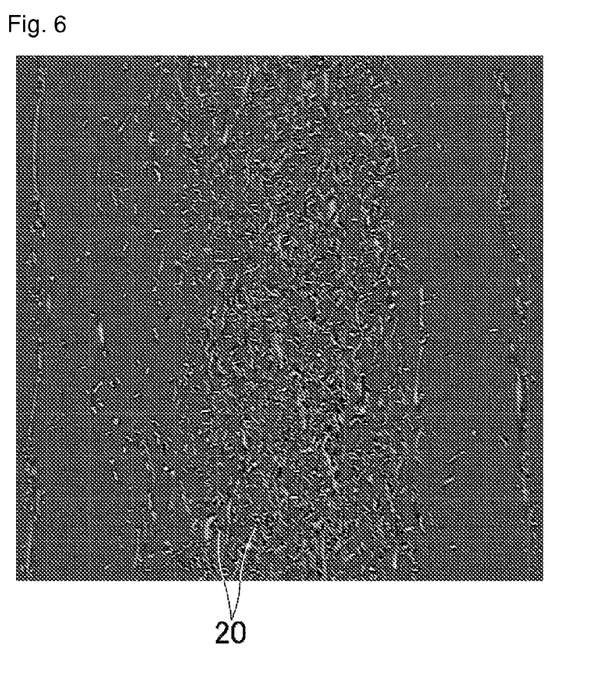
FIG. 6 is still another exemplary X-ray CT photo.
Figure 7:
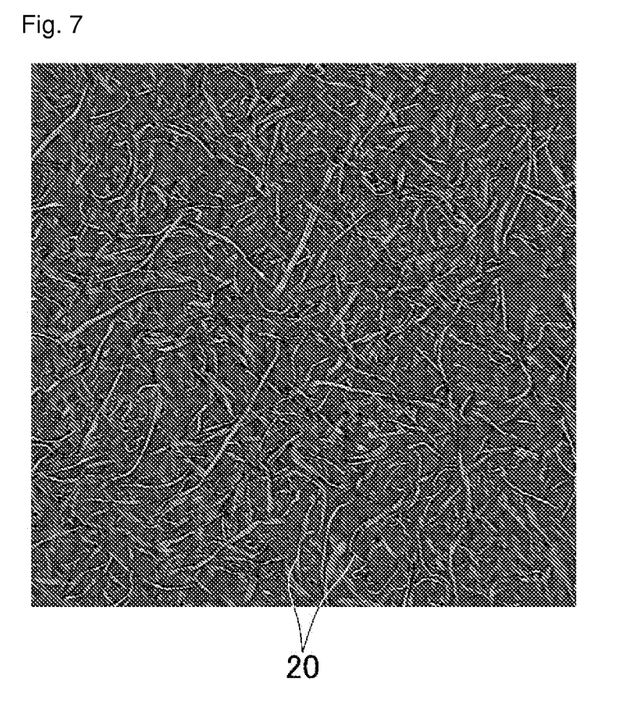
FIG. 7 is yet another exemplary X-ray CT photo.

FIGS. 4, 5, 6 and 7 exemplarily show several X-ray CT photographs. FIG. 4 is a stereoimage of a test piece cut from the core material 11 according to EXAMPLE 1 described later to be X-ray CT photographed wherein coordinate axes corresponding to X-, Y- and Z-axes in FIG. 3 are also indicated. FIG. 5 is a photograph of the XY cross-section in which the cross-sections of many component fibers constituting the fluff wood pulp fibers 20 appear. FIG. 6 is a photograph of the YZ cross-section and, also in this photograph, cross-sections of many component fibers constituting the fluff wood pulp fibers 20 appear. FIG. 7 is a photograph of the XZ cross-section and, also in this photograph, cross-sections of many component fibers constituting the fluff wood pulp fibers 20 appear.

From the X-ray CT photographs exemplarily shown by FIGS. 5 through 7 prepared on the basis of FIGS. 3(a), 3(b) and 3(c), cross-sectional areas and average cross-sectional areas of the fluff wood pulp fibers are obtained by the procedures as will be described below.

(1) Images of the XY cross-section, the YZ cross-section and the XZ cross-section are obtained in the form of bit map files and respective cross-sectional images are blitted to the image analysis software "USB digital scale" developed by Scalar Corporation.

(2) A bit map file image of a region to be measured is clipped out. The object to be clipped out is a range of about ⅓ of the thickness in a central region of the core material as viewed in the thickness direction in the case of the XY cross-section and the YZ cross-section, and a range of about 500 pixels x about 500 pixels in the case of the XZ cross-section.

(3) The images obtained are binarized and the cross-sectional regions of the fluff wood pulp fibers in the respective cross-sections are made extractable.

(4) Area ratios of the fluff wood pulp fibers 20 in the respective cross-sections are calculated and it is confirmed that the area ratio is generally common to the XY cross-section, the YZ cross section and the XZ cross-section.

(5) A lower limit of element extraction range is set to $2 \times 10^{-10}$ m$^2$ converted in the cross-sectional area of the fluff wood pulp fibers and a cross-sectional area of the fluff wood pulp fibers 20 smaller than this lower limit excluded from the element extraction.

(6) Average numbers of pixels in the cross-sections of fluff wood pulp fibers element extracted in the respective cross-sections are counted.

(7) The horizontal orientation indices are calculated according to the following formula:

Horizontal orientation index=(average number of pixels in XZ cross-section)/((average number of pixels in XY cross-section+average number of pixels in YZ cross-section)/2)

and the value obtained is adopted as the horizontal orientation index $I_H$ of the fluff wood pulp fibers 20. The term "average number of pixels" in the above-described formula may also be referred to as "average value of cross-section of the fluff wood pulp". Expression "the horizontal orientation index is large" means that a large quantity of the fluff wood pulp fibers is oriented in the horizontal direction.

The fluff wood pulp fibers 20, air-conveyed and sandwiched between the carrier sheet web 15a and the cover sheet web 13a in laminated but not compressed state to form the first composite laminate web 26 is then sandwiched, in the fourth step IV in FIG. 2, between a pair of air-permeable supporting members, i.e., the second endless belt 27 and the third endless belt 28 spaced from each other by the distance $d_1$. In this fourth step IV, the fluff wood pulp fibers 20 is injected with high-pressure steam jets and, in consequence, the fluff wood pulp fibers 20 having extended in the horizontal direction in the XZ cross-section before being injected with steam jets is reoriented in the XY cross-section and the YZ cross-section after being injected with high-pressure steam jets. By increasing a percentage of the component fibers of the fluff wood pulp fibers 20 oriented in the thickness direction TD (See FIG. 3) of the core material 11, it is possible to facilitate bodily fluids to disperse and to penetrate toward the outer surface 14 without staying on the inner surface 12 of the core material 11. In the bodily fluid-absorbent structure 10 in which the core material 11 functions in this manner, the cover sheet 13 as well as the topsheet 2 can be easily maintained in dry condition and the menstruation napkin 1 would not cause the wearer's discomfort due to a wet state of the topsheet 2.

The inventors have recognized that, generally, in a core material containing fluff wood pulp fibers generally oriented not in the thickness direction of the core material, when the inner surface of the region having a low density, in other words, the region having a large specific volume is wetted with bodily fluids, wood pulp fibers will get closer one to another under the effect of cohesive force and mass of bodily fluids and this region will be densified. Compared to such region, the low-density region defined around the densified region is generally not wetted with the bodily fluids and, in this low-density region, the wood pulp fibers do not get closer one to another and make it difficult for bodily fluids to disperse thereinto. Consequentially, in the high-density region wetted with bodily fluid, the inner surface will sink and sometimes will make for undesirable staying of bodily fluids.

Such problem is overcome or at least reduced by the core material 11 according to one or more embodiments of the present invention which promotes dispersion and penetration of bodily fluids from the inner surface 12 toward the outer surface 14 to restrict sinking of the inner surface 12 and thereby to restrict staying of bodily fluids.

To obtain the core material 11 and the bodily fluid-absorbent structure 10 functioning in the manner as has been described above, the core material 11 having a basis mass in a range of 150 to 500 g/m² is used according to one or more embodiments of the present invention. The core material having a basis mass lower than 150 g/m² will lack in practicality. The core material having a basis mass exceeding 500 g/m² will make it difficult to orient the component fibers of fluff wood pulp fibers 20 in the thickness direction TD of the core material 11 at high efficiency under injection of high-pressure steam jets. For the desired function, the core material 11 preferably has a specific volume in a range of 3 to 20 cc/g. The core material 11 of specific volume in such range has flexibility appropriate to be used in bodily fluid-absorbent articles, such as menstruation napkins. In addition, for the core material 11 in some embodiments, the relationship between the specific volume VSP and the horizontal orientation index $I_H$ satisfies the following formula:

$I_H$ is less than or equal to $-0.099\text{VSP}+2.4$.

where VSP is measured in cc/g.

As will be apparent from TABLES 1 and 2 and FIG. 8 referred to hereinafter in detail, in the core material 11 having the horizontal orientation index $I_H$ in this range, it was experimentally observed the fluff wood pulp fibers 20 is oriented in the thickness direction TD of the core material 11 and facilitates bodily fluids to disperse and permeate in the core material 11 from the inner surface 12 thereof toward the outer surface 14. In such core material 11, a dispersion area $S_A$ of artificial menstrual blood on the inner surface 12 measured 20 seconds after 0.3 ml of artificial menstrual blood had been dropped on the inner surface 12 was smaller than a dispersion area $S_B$ of artificial menstrual blood on the outer surface 14 measured 3 minutes after the dispersion area $S_A$ had been measured. (See EXAMPLES 1 through 4 and TABLE 2 referred to hereinafter).

By restricting staying of bodily fluids on the inner surface 12 of the core material 11, uncomfortable feeling experienced by the wearer of the menstruation napkin 1 when the inner surface 12 comes in contact via the topsheet 2 with the wearer's skin can be effectively alleviated. As means to confirm such effect, the inventors used "KES-77 high-accuracy and high-speed thermal property measuring device THERMO-LABO II" manufactured by KATO TECH CO., LTD. In the measurement conducted using this device, the artificial menstrual blood and the core material were conditioned for 48 hours within a room atmosphere set at a temperature of 20° C. and a relative humidity of 75% and a sensor associated with the device was set at 30° C. The sensor was put in contact with the inner surface 12 of the core material 11 having been dropped with artificial menstrual blood and a peak value Qmax of heat transfer between the sensor and the inner surface 12 for a predetermined duration was measured. As one of specific examples of the sensor, a copper plate having an area of 9 cm² and a mass of 9.79 g was used and heat energy was accumulated in this copper plate so that the copper plate may be maintained at a predetermined temperature, for example, of 30° C. A peak value of heat flow designated as Qmax immediately after the sensor had come in contact with the inner surface 12 was measured. This peak value Qmax has been considered to be a reference value indicating a degree of cold or warm sense the wearer experiences when her skin comes in contact with an object, e.g., a sanitary napkin. Specifically, at a larger Qmax, cold sense will be significant and, at a smaller Qmax, warm sense will be significant. The core material 11 according to one or more embodiments of the present invention is able to restrict staying of bodily fluids on the inner surface 12 and Qmax can be correspondingly reduced to avoid a possibility that the wearer of the menstruation napkin might experience uncomfortable cold sense. It should be noted here that the core material 11 and menstrual blood are at generally the same temperature when the core material 11 is practically absorbing menstrual blood being excreted in the menstruation napkin put on the wearer's body. In such situation, if Qmax of the core material 11 is relatively large, the wearer of the menstruation napkin will experience a sense of uncomfortable wetness and/or soiling due to delayed absorption of menstrual blood rather than a feel of cold.

Measurement items to evaluate the core material 11 obtained according to one or more embodiments of the present invention will be described below: (1) thickness, (2) basis mass, (3) horizontal orientation index $I_H$, (4) variation of cross-sectional area after drip of artificial menstrual blood, (5) dispersion area of artificial menstrual blood on the inner surface, (6) dispersion area of artificial menstrual blood on the outer surface and (7) Qmax Measuring methods for these measurement items will be described below.

(1) Thickness a. The bodily fluid-absorbent structure was cut into a size of 10×10 mm and the cover sheet was peeled off to obtain test pieces for measurement. A dial thickness gauge was used to measure a thickness of the test piece. A probe having a diameter of 50 mm was used and a measuring load was set to 2.5/cm².

b. Thickness measurement was conducted on ten test pieces and an average value of measured ten values was adopted as the thickness of the core material.

(2) Basis Mass a. A test piece obtained in the same manner as in (1) was weighed and a basis mass was calculated according to the following formula:

Basis mass (g/m²)=measured mass (g)/0.01(m²)

(3) Horizontal Orientation Index $I_H$ a. The method having been described in reference to FIG. 3 was used.

(4) Variation of Cross-Sectional Area After Drip of Artificial Menstrual Blood, (5) Dispersion Area of Artificial Menstrual Blood on the Inner Surface and (6) Dispersion Area of Artificial Menstrual Blood on the Outer Surface a. A test piece obtained in the same manner as in (1) was used.

b. Measurement apparatus: 2D Laser Displacement Sensor manufactured by Keyence Corporation. This apparatus includes primary instruments as follow.

Sensor head: LJ-G030 (laser oscillation and measurement head) manufactured by Keyence Corporation.

Controller: LJ-5000 set (data collection and storage) manufactured by Keyence Corporation.

LCD monitor: CA-MP81 manufactured by Keyence Corporation.

With these instruments, laser reflection may be used to 2D-measure (according to coordinates in alignment one to another in the height direction) a surface profile of the test piece and data obtained in this manner may be stored. To extract the coordinates in the height direction, the application software "LJ Navigator (version 1.5.1.0" was used and, for adding-up and calculation of cross-sectional area variation, data was transferred to the spreadsheet software "EXCEL 2003" of Microsoft Corporation.

c. The test piece was set on 2D Laser Displacement Sensor to measure surface irregularities.

d. 0.3 ml of the artificial menstrual blood was dropped for one second to a center of the region in which the irregularities had been measured.

e. 20 seconds after the drop of the artificial menstrual blood, the irregularities was measured again in the region in which the previous measurement of the irregularities had been conducted.

f. Immediately after the measurement described in the measurement item e, a straight ruler was used to measure a dimension of the inner surface soiled with the artificial menstrual blood in the machine direction MD and the cross direction CD in the process of making the core material.

g. Ellipsoidal equivalent was calculated from the dimension measured by the item f to obtain a dispersion area $S_A$ of the artificial menstrual blood on the inner surface.

h. The coordinate value measured in the item c was subtracted from the coordinate value measured in the item e, then the subtraction result was multiplied by the measurement pitch (0.033 mm) and finally the multiplication result was integrated to obtain the cross-sectional variation before and after absorption of the artificial menstrual blood.

i. The outer surface of the core material was observed 3 minutes after the drip of the artificial menstrual blood and dimensions in orthogonal two directions of the region visually recognized on and through the outer surface to be soiled with the artificial menstrual blood were measured and the dimensions measured were elliptically converted to obtain the dispersion areas. Of the dispersion areas obtained in this manner, the dispersion area being larger was adopted as the dispersion area $S_B$ of the artificial menstrual blood on the outer surface.

j. Composition of artificial menstrual blood:
a. ion-exchanged water 1 L
b. glycerin 80 g
c. carboxymethylcellulose sodium 8 g
d. sodium chloride 10 g
e. sodium hydrogen carbonate 4 g
f. pigment Red No. 102 8 g
g. pigment Red No. 2 2 g
h. pigment Red No. 5 2 g
Ingredients b through e were added to ingredient a and agitated for 3 hours. Then, ingredients f through h were added and agitated for 1 hour to obtain the artificial menstrual blood.

(7) Qmax
a. The test piece was obtained by the same method as used in (1).
b. Measurement apparatus: "KES-F7 high-accuracy and high-speed thermal property measuring device THERMO-LABO II" manufactured by KATO TECH CO., LTD. was used. The sensor of "THERMOLABO II" was weighted, in addition to standard weighting, so that a contact pressure may be set to 30 g/m².
c. Drip quantity of the artificial menstrual blood: Assuming cylinders respectively having a diameter of 18mm and heights corresponding to thickness of the test pieces obtained from the core materials according to EXAMPLES 1 through 4, quantities of the artificial menstrual blood corresponding to ⅔ of volumes of the respective cylinders were dropped to the respective test pieces for one second. Quantities of the artificial menstrual blood actually having been dropped to the respective test pieces were as described below:

EXAMPLE 1: 0.16 ml
EXAMPLE 2: 0.33 ml
EXAMPLE 3: 0.5 ml
EXAMPLE 4: 0.83 ml d. Sequence of measurement was as described below:
(a) "THERMOLABO II" was set to a predetermined temperature.
(b) Predetermined quantity of the artificial menstrual blood was dropped to the central region of the test piece for 1 minute.
(c) 10 seconds after the drip, the center of the sensor associated with "THERMOLABO II" was placed on the center of the region to which the artificial menstrual blood had been dropped, then the sensor was applied with a load of 30 g/cm² to measure a peak value Qmax of heat transfer between the test piece and the sensor.
(d) Measured values on the three test pieces were averaged to obtain the Qmax of the core material.

EXAMPLES

Examples 1 through 4

Parameters as described below were applied to the process illustrated by FIG. 2 and the distance $d_1$ between the second endless belt and the third endless belt were appropriately changed in a range of 0.4 to 2.4 mm to obtain EXAMPLES 1 through 4 of the core material used in the bodily fluid-absorbent structure of the menstruation napkin. On EXAMPLES 1 through 4 of the core material, thickness, basis mass, horizontal orientation index $I_H$, cross-sectional area variation after drip of artificial menstrual blood, dispersion area of artificial menstrual blood on the inner surface, dispersion area of artificial menstrual blood on the outer surface and Qmax value were measured and results of measurement were recorded in TABLES 1 and 2.

(1) Fluff wood pulp: NB-416 manufactured by Weyorhaeuser
(2) Quantity of fluff wood pulp fibers consumed per unit core material: 300 g/m²
(3) Carrier sheet and cover sheet: Air-through nonwoven fabric formed of corein-sheath type conjugate fibers consisting of polyester as the core and polyethylene as the sheath. Basis mass of the nonwoven fabric is 25 g/m², fineness of the nonwoven fabric is 2.2 dtex and fiber length of the nonwoven fabric is 51 mm.
(4) Running rate of carrier sheet and cover sheet: 5 m/min.
(5) Diameter of steam injection nozzle: 0.5 mm.
(6) Pitch at which the steam nozzles are arranged: 2 mm.
(7) Steam pressure: 0.7 Mpa.
(8) Quantity of steam injected to first wood pulp fibers unit (quantity for steam treatment): 1.27 kg/m².

Examples 5, 6

EXAMPLES 5 and 6 of the core material and the test pieces for measurement thereof were obtained by the method similar to that for EXAMPLE 1 except that 500 g/m² (EXAMPLE 5) or 200 g/m² (EXAMPLE 6) of fluff wood pulp fibers was used and the distance $d_1$ between the second endless belt and the third endless belt was set to 2.4 mm (EXAMPLE 5) or 0.5 mm (EXAMPLE 6). On the test pieces, thickness, basis mass, cross-sectional variation after drip of the artificial menstrual blood, dispersion area of the artificial menstrual blood on the inner surface, dispersion area of the artificial menstrual blood and Qmax were measured and measurement results as seen in TABLES 1 and 2 were obtained.

Example 7

EXAMPLE 7 of the core material and test pieces for measurement thereof was obtained by the method similar to that for EXAMPLE 2 except that Super-soft IP-SS manufactured by International Paper Company was used as fluff wood pulp. On the test pieces, measurement similar to that for EXAMPLES 5 and 6 was conducted and measurement results as seen in TABLES 1 and 2 were obtained.

Examples 8, 9

EXAMPLES 8 and 9 of the core material and test pieces for measurement were obtained by the method similar to that used for EXAMPLE 2 except that the fluff wood pulp fibers used for EXAMPLE 1 was replaced by composite liquid-absorbent material consisting of the fluff wood pulp fibers mixed with the super-absorbent polymer particles at a rate of 200 g/m². On the core material obtained, the measurements similar to those conducted for EXAMPLES5 and 6 were conducted and the results as seen in TABLES 1 and 2 were obtained. As the super-absorbent polymer particles, UG-860D manufactured by SUMITOMO SEIKA Chemicals Co., Ltd. and UP-270 manufactured by San-Dia Polymer, Ltd. were used.

COMPARATIVE EXAMPLES

Comparative Examples 1 through 4

Injection of high-pressure steam jets to the first composite laminate web in the step IV of the process illustrated by FIG. 2 used to obtain EXAMPLES 1 through 4 of the core material was replaced by mechanically compressing the first composite laminate web running in the machine direction MD at a rate of 5 m/min by a pair of press rolls to obtain COMPARATIVE EXAMPLES 1 through 4 of the core material having thickness comparable to thickness of EXAMPLES 1 through 4 of the core material. Each of the press rolls had a diameter of 250 mm. By varying the roll peripheral surface distance was appropriately varied to vary the thickness of the core material in the respective COMPARATIVE EXAMPLES. From COMPARATIVE EXAMPLES of the core material, test pieces for measurement were prepared by the same method as in the case of EXAMPLE 1. On the respective test pieces, the measurement similar to that conducted for EXAMPLES 1 through 4 was conducted and the results as seen in TABLES 1 and 2 were obtained.

Comparative Examples 5, 6

The first composite laminate web 26 of FIG. 2 used in the course of obtaining EXAMPLES 5 and 6 was compressed by the paired press roll similar to those used to make COMPARATIVE EXAMPLE 1 of the core material to obtain COMPARATIVE EXAMPLES 5 and 6 of the core material having thickness comparable to that of EXAMPLES 5 and 6 and test pieces thereof. Measurement similar to that conducted on EXAMPLES 5 and 6 was conducted and results as seen in TABLES 1 and 2 were obtained.

Comparative Example 7

The first composite laminate web 26 used in the process for making the core material according to EXAMPLE 7 was compressed by a pair of press rolls similar to those used to obtain COMPARATIVE EXAMPLE 1 of the core material having thickness comparable to EXAMPLE 7 and test piece thereof. The measurement similar to that EXAMPLE 7 was conducted and results as seen in TABLES 1 and 2 were obtained.

Comparative Examples 8, 9

The core material and the test piece for measurement were obtained in the same manner as in COMPARATIVE EXAMPLE 2 except that the fluff wood pulp fibers used in COMPARATIVE EXAMPLE 2 was replaced by composite liquid-absorbent material consisting of the fluff wood pulp fibers mixed with the super-absorbent polymer particles at a rate of 200 g/m². On the test piece, measurement similar to that in COMPARATIVE EXAMPLES 5 and 6 was conducted and results as seen in TABLES 1 and 2 were obtained.

TABLE 1

| | Fluff wood pulp fibers | Quantity of fluff wood pulp fibers (g/m²) | Super-absorbent polymer particles | Quantity of super-absorbent polymer particles (g/m²) | Use of high-pressure steam jets or press rolls | Distance d1 between the belts Distance d2 between the rolls | Thickness of core material (mm) | Basis mass (g/m²) | Specific volume $V_{SP}$ (cc/g) | Horizontal orientation index $I_H$ |
|---|---|---|---|---|---|---|---|---|---|---|
| EXAMPLE 1 | NB416 | 300 | None | | high-pressure steam jets | 0.4 | 1.1 | 304.3 | 3.61 | 2.07 |
| EXAMPLE 2 | NB416 | 300 | None | | high-pressure steam jets | 1.3 | 2.1 | 282.8 | 7.43 | 1.55 |
| EXAMPLE 3 | NB416 | 300 | None | | high-pressure steam jets | 1.9 | 3.4 | 305.6 | 11.13 | 1.22 |
| EXAMPLE 4 | NB416 | 300 | None | | high-pressure steam jets | 2.4 | 4.5 | 300.0 | 15.00 | 0.93 |
| COMPARATIVE EXAMPLE 1 | NB416 | 300 | None | | press rolls | 0.2 | 1.0 | 278.6 | 3.59 | 2.40 |
| COMPARATIVE EXAMPLE 2 | NB416 | 300 | None | | press rolls | 0.35 | 1.9 | 304.5 | 6.24 | 1.92 |
| COMPARATIVE EXAMPLE 3 | NB416 | 300 | None | | press rolls | 0.6 | 3.5 | 279.0 | 12.54 | 1.47 |
| COMPARATIVE EXAMPLE 4 | NB416 | 300 | None | | press rolls | 0.8 | 5.2 | 279.1 | 18.63 | 1.05 |
| EXAMPLE 5 | NB416 | 500 | None | | high-pressure steam jets | 2.4 | 3.3 | 460.4 | 7.17 | — |

TABLE 1-continued

| | Fluff wood pulp fibers | Quantity of fluff wood pulp fibers (g/m²) | Super-absorbent polymer particles | Quantity of super-absorbent polymer particles (g/m²) | Use of high-pressure steam jets or press rolls | Distance d1 between the belts Distance d2 between the rolls | Thickness of core material (mm) | Basis mass (g/m²) | Specific volume $V_{SP}$ (cc/g) | Horizontal orientation index $I_H$ |
|---|---|---|---|---|---|---|---|---|---|---|
| EXAMPLE 6 | NB416 | 200 | None | | high-pressure steam jets | 0.5 | 1.4 | 193.3 | 7.24 | — |
| EXAMPLE 7 | IP-SS | 300 | None | | high-pressure steam jets | 1.05 | 2.1 | 287.3 | 7.31 | — |
| EXAMPLE 8 | NB416 | 300 | UG-860D | 200 | high-pressure steam jets | 0.5 | 2 | 460.0 | 4.35 | — |
| EXAMPLE 9 | NB416 | 300 | UG-270 | 200 | high-pressure steam jets | 0.5 | 2 | 468.4 | 4.27 | — |
| COMPARATIVE EXAMPLE 5 | NB416 | 500 | None | | press rolls | 0.7 | 4 | 427.3 | 9.36 | — |
| COMPARATIVE EXAMPLE 6 | NB416 | 200 | None | | press rolls | 0.35 | 1.5 | 174.2 | 8.61 | — |
| COMPARATIVE EXAMPLE 7 | IP-SS | 300 | None | | press rolls | 0.25 | 2.2 | 292.9 | 7.51 | — |
| COMPARATIVE EXAMPLE 8 | NB416 | 300 | UG-860D | 200 | press rolls | 0.35 | 2 | 413.5 | 4.84 | — |
| COMPARATIVE EXAMPLE 9 | NB416 | 300 | UG-270 | 200 | press rolls | 0.35 | 2.1 | 463.2 | 4.53 | — |

TABLE 2

| | Measurement of Qmax | | | Dispersion of artificial menstrual blood | | |
|---|---|---|---|---|---|---|
| | The amount of dropped artificial menstrual blood (cc) | The load applied onto the sensor (g/cm²) | Qmax | Dispersion area on inner surface $S_A$ (mm²) | Dispersion area on outer surface $S_B$ (mm²) | Variation of cross-sectional area (mm²) |
| EXAMPLE 1 | 0.16 | 30 | 0.174 | 174.2 | 604.8 | 10.5 |
| EXAMPLE 2 | 0.33 | 30 | 0.185 | 136.8 | 431.9 | 2.2 |
| EXAMPLE 3 | 0.5 | 30 | 0.142 | 134.7 | 202.5 | −12.5 |
| EXAMPLE 4 | 0.83 | 30 | 0.161 | 122.5 | 127.3 | −23.1 |
| COMPARATIVE EXAMPLE 1 | 0.16 | 30 | 0.388 | 462.8 | 525.4 | 9.7 |
| COMPARATIVE EXAMPLE 2 | 0.33 | 30 | 0.390 | 237.1 | 252.2 | 2.4 |
| COMPARATIVE EXAMPLE 3 | 0.5 | 30 | 0.399 | 178.4 | 8.8 | −22.2 |
| COMPARATIVE EXAMPLE 4 | 0.83 | 30 | 0.562 | 162.8 | 0.0 | −35.6 |
| EXAMPLE 5 | 0.55 | 30 | 0.186 | 147.4 | 180.8 | 6.0 |
| EXAMPLE 6 | 0.2 | 30 | 0.244 | 151.7 | 521.0 | 15.4 |
| EXAMPLE 7 | 0.33 | 30 | 0.293 | 183.7 | 358.2 | 5.6 |
| EXAMPLE 8 | 0.33 | 30 | 0.260 | 167.3 | 295.1 | 12.4 |
| EXAMPLE 9 | 0.33 | 30 | 0.262 | 160.5 | 317.3 | 10.0 |
| COMPARATIVE EXAMPLE 5 | 0.2 | 30 | 0.436 | 247.6 | 9.5 | −5.8 |
| COMPARATIVE EXAMPLE 6 | 0.33 | 30 | 0.373 | 215.0 | 420.6 | −7.1 |
| COMPARATIVE EXAMPLE 7 | 0.33 | 30 | 0.452 | 221.4 | 230.3 | 1.3 |
| COMPARATIVE EXAMPLE 8 | 0.33 | 30 | 0.336 | 206.0 | 261.3 | 6.0 |
| COMPARATIVE EXAMPLE 9 | 0.33 | 30 | 0.319 | 298.5 | 232.2 | 10.2 |

Figure 8:
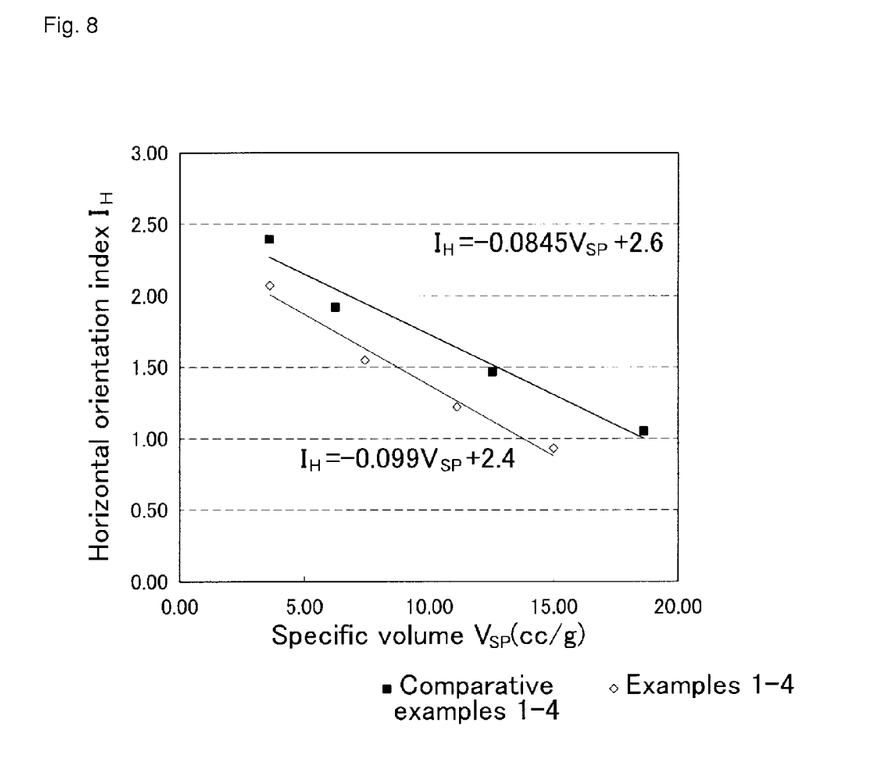
FIG. 8 is a graphic diagram plotting a relationship between a specific volume and a horizontal orientation index of a bodily fluid-absorbent structure.

FIG. 8 is a graphic diagram plotting the specific volume vs the horizontal orientation index in EXAMPLES 1 through 4 and COMPARATIVE EXAMPLES 1 through 4. For EXAMPLES 1 through 4 of the core material, a relationship between the specific volume $V_{SP}$ and the horizontal orientation index L was able to be represented by the following formula.

$$I_H = -0.099 V_{SP} + 2.4$$

where Vsp is measured in cc/g.

In COMPARATIVE EXAMPLES 1 through 9 of the core material, relationship between the specific volume $V_{SP}$ and the horizontal orientation index $I_H$ was able to be represented by the following formula.

$$I_H = -0.0845 V_{SP} + 2.6$$

where Vsp is measured in cc/g.

Assume that the specific volume is the same, a percentage at which the fluff wood pulp fibers in the core material may be oriented in the horizontal direction was lower in EXAMPLES 1 through 4 than in COMPARATIVE EXAMPLES 1 through 4, respectively. In the case of the core material containing the super-absorbent polymer particles, a value obtained by subtracting the volume occupied by the super-absorbent polymer particles from the volume of the core material was used to calculate the specific volume of the core material.

Figure 9:
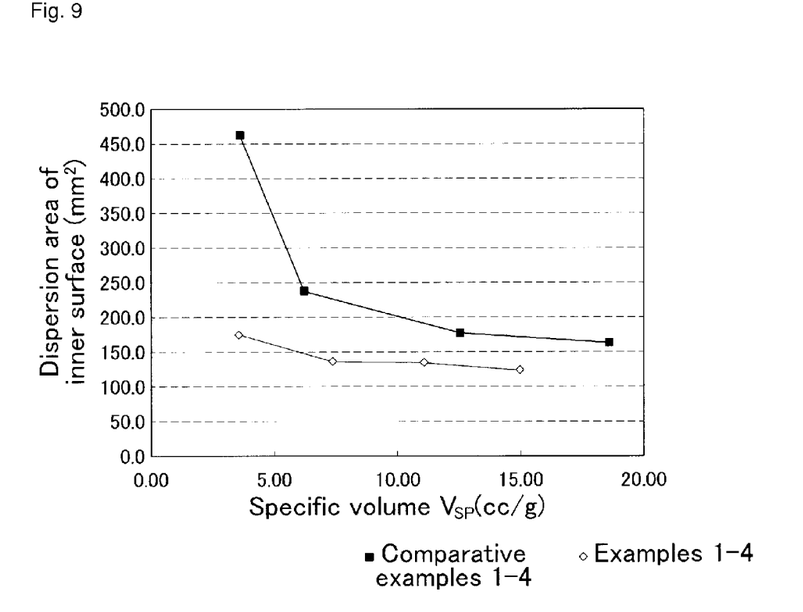
FIG. 9 is a graphic diagram plotting a relationship between a specific volume and a dispersion area on the inner surface of a bodily fluid-absorbent structure.

FIG. 9 is a graphic diagram plotting the specific volume vs the dispersion area on the inner surface in EXAMPLES 1 through 4 and COMPARATIVE EXAMPLES 1 through 4. Assume that the specific volume of the core material is the same, the dispersion area on the inner surface was apt to be smaller in EXAMPLES 1 through 9 than in COMPARATIVE EXAMPLES 1 through 9, respectively.

Figure 10:
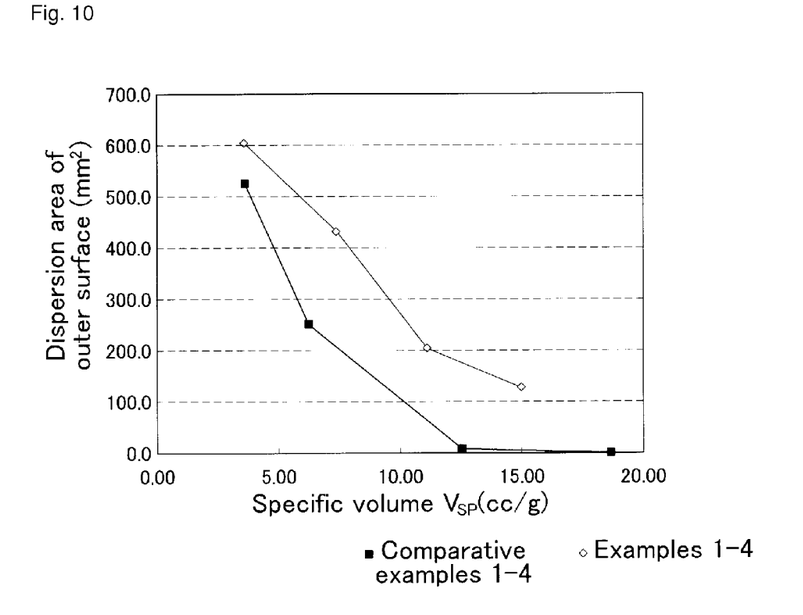
FIG. 10 is a graphic diagram plotting a relationship between a specific volume and a dispersion area on the outer surface of a bodily fluid-absorbent structure.

FIG. 10 is a graphic diagram plotting specific volume vs dispersion area on the outer surface in EXAMPLES 1 through 4 and COMPARATIVE EXAMPLES 1 through 4. Assume that the specific volume of the core material is the same, the dispersion area on the outer surface was apt to be larger in EXAMPLES 1 through 9 than in COMPARATIVE EXAMPLES 1 through 9, respectively.

Figure 11:
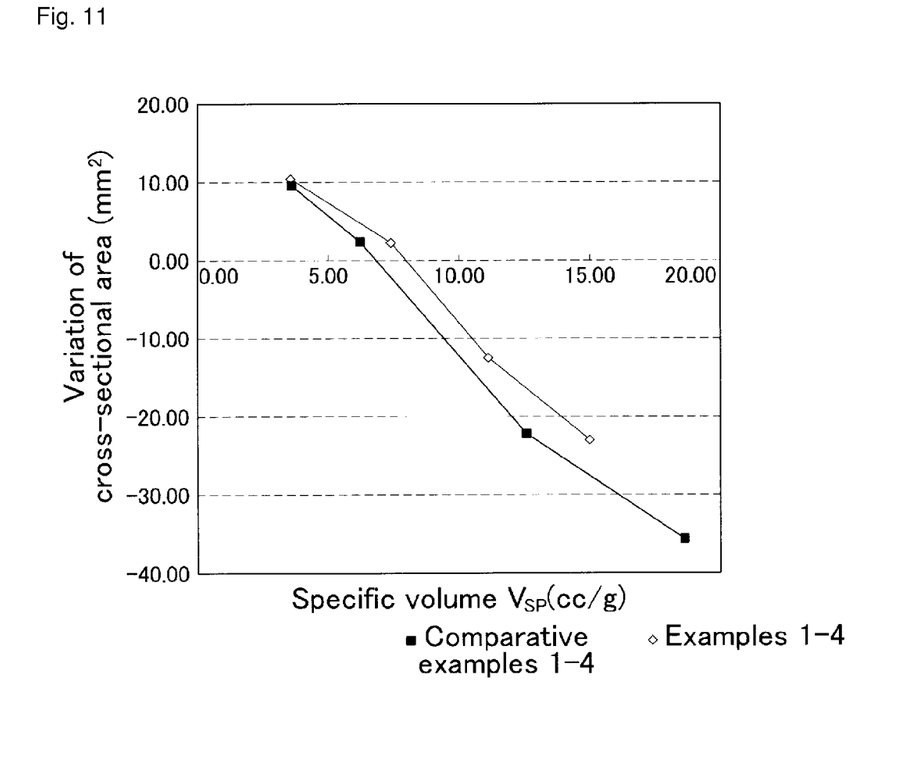
FIG. 11 is a graphic diagram plotting a relationship between a specific volume and a variation in cross-sectional area of a bodily fluid-absorbent structure.

FIG. 11 is a graphic diagram plotting specific volume vs cross-sectional area variation in EXAMPLES 1 through 4 and COMPARATIVE EXAMPLES 1 through 4 in TABLES 1 and 2. Assume that the specific volume of the core material is the same, the cross-sectional area variation was apt to be smaller in EXAMPLES 1 through 9 than in COMPARATIVE EXAMPLES 1 through 9, respectively.

The first aspects described above may be arranged in at least the following items:

(i) A bodily fluid-absorbent structure comprising liquid-absorbent material formed of an aggregation of fluff wood pulp fibers and having an inner surface and an outer surface, a liquid-pervious sheet covering the inner surface and a liquid-pervious or liquid-impervious sheet covering the outer surface, the bodily fluid-absorbent structure being characterized in that:

the aggregation has a basis mass in a range of 150 to 500 g/m² and a specific volume in a range of 3 to 20 cc/g;

a relationship between a horizontal orientation index L and the specific volume $V_{SP}$ of the fluff wood pulp fibers in the aggregation is represented by a formula $I_H$ is less than or equal to $-0.099 VSP + 2.4$ and the horizontal orientation index $I_H$ is a value obtained according to a formula $I_H = CS_1 / ((CS_2 + CS_3)/2)$ wherein $CS_1$ represents an average cross-sectional area of the fluff wood pulp fibers observed on a cross-section extending in parallel to a horizontal plane when the outer surface of the aggregation is placed on the horizontal plane, $CS_2$ and $CS_3$ represent average cross-sectional areas of the fluff wood pulp fibers observed on two cross-sections extending orthogonally to each other and to the horizontal plane.

One or more aspect described in the above item (i) may provide one or more of the following advantageous effects:

A horizontal orientation index $I_H$ in the aggregation of fluff wood pulp fibers used as the primary core material for the bodily fluid-absorbent structure is reduced to a value as low as possible and thereby a percentage of fluff wood pulp fibers extending in the direction which is orthogonal to a horizontal place is increased to a value as high as possible so that the planar dispersion of bodily fluids over a wide range on the upper surface of the structure may be effectively restricted and dispersion from the inner surface to the outer surface of the structure may be promoted.

Additionally, one or more of the following embodiments are provided in accordance with further aspects:

(ii) (a) a dispersion area $S_A$ of artificial menstrual blood on the inner surface 20 seconds after 0.3 ml of the artificial menstrual blood was dropped onto the inner surface of the aggregation is smaller than (b) a dispersion area $S_B$ of the artificial menstrual blood on the outer surface 3 minutes after 0.3 ml of the artificial menstrual blood was dropped onto the inner surface of the aggregation.

(iii) The aggregation includes the fluff wood pulp fibers and the super-absorbent polymer particles and the specific volume is the value calculated by subtracting a volume of the super-absorbent polymer particles from the aggregation including the super-absorbent polymer particles.

(iv) The aggregation is obtained by sandwiching the fluff wood pulp fibers between a pair of air-permeable support means spaced from each other by a predetermined distance, injecting high-pressure steam jets to the aggregation from the outside of one of the pair of support means and sucking the high-pressure steam jets from the outside of the other of the pair of support means.

(v) The aggregation includes super-absorbent polymer particles.

(vi) The average values $CS_1$, $CS_2$ and $CS_3$ of the cross-sections of the fluff wood pulp fibers are values obtained from X-ray CT photographs of the aggregation.

According to the embodiments in the above (ii) to (vi), the advantageous effect(s) set forth at (a) is/are better ensured. Further advantageous effects of the respective embodiments may be obtained as discussed in the respective related descriptions. The entire disclosure of Japanese Patent Application No. 2010-084216 filed on Mar. 31, 2010 including specification, drawings and abstract is herein incorporated by reference in its entirety.

The invention claimed is:

1. A bodily fluid-absorbent structure, comprising
   liquid-absorbent material formed of an aggregation of fluff wood pulp fibers and having an inner surface and an outer surface,
   a liquid-pervious sheet covering said inner surface, and
   a liquid-pervious or liquid-impervious sheet covering said outer surface,
   wherein
      said aggregation has a basis mass in a range of 150 to 500g/m² and a specific volume in a range of 3 to 20 cc/g;
      a relationship between a horizontal orientation index $I_H$ and said specific volume VSP of said fluff wood pulp fibers in said aggregation is represented by the following formula $I_H$ is less than or equal to $-0.099 VSP + 2.4$ and
   said horizontal orientation index $I_H$ is a value obtained according to the following formula $I_H = CS_1 / ((CS_2 + CS_3)/2)$ where
   $CS_1$ represents an average cross-sectional area of said fluff wood pulp fibers observed on a cross-section extending in parallel to a horizontal plane when said outer surface of said aggregation is placed on said horizontal plane,
   $CS_2$ and $CS_3$ represent average cross-sectional areas of said fluff wood pulp fibers observed on two cross-sections extending orthogonally to each other and to said horizontal plane.

2. The bodily fluid-absorbent structure defined by claim 1, wherein (a) a dispersion area $S_A$ of artificial menstrual blood on said inner surface 20 seconds after 0.3ml of the artificial menstrual blood was dropped onto said inner surface of said aggregation is smaller than (b) a dispersion area $S_B$ of the artificial menstrual blood on said outer surface 3 minutes after said 0.3ml of the artificial menstrual blood was dropped onto said inner surface of said aggregation.

3. The bodily fluid-absorbent structure defined by claim 1, wherein
said aggregation includes said fluff wood pulp fibers and super-absorbent polymer particles, and said specific volume is the value calculated by subtracting a volume of said super-absorbent polymer particles from a volume of said aggregation including said super-absorbent polymer particles.

4. The bodily fluid-absorbent structure defined by claim 1, wherein said aggregation is obtained by sandwiching said fluff wood pulp fibers between a pair of air-permeable support members spaced from each other by a predetermined distance, injecting high-pressure steam jets to said aggregation from the outside of one of said pair of support members and sucking said high-pressure steam from the outside of the other of said pair of support members.

5. The bodily fluid-absorbent structure defined by claim 4, wherein said aggregation includes super-absorbent polymer particles.

6. The bodily fluid-absorbent structure defined by claim 1, wherein the average values $CS_1$, $CS_2$ and $CS_3$ are values obtained from X-ray CT photographs of said aggregation.

7. The bodily fluid-absorbent structure defined by claim 4, wherein said predetermined distance is between 0.4 and 2.4 mm.

* * * * *